US011504198B2

(12) United States Patent
Tojo et al.

(10) Patent No.: US 11,504,198 B2
(45) Date of Patent: Nov. 22, 2022

(54) SURGICAL SYSTEM AND METHOD FOR CONTROLLING THE SAME

(71) Applicants: KAWASAKI JUKOGYO KABUSHIKI KAISHA, Kobe (JP); MEDICAROID CORPORATION, Kobe (JP)

(72) Inventors: Tsuyoshi Tojo, Ibaraki (JP); Kenji Noguchi, Kobe (JP); Tetsushi Ito, Kobe (JP); Tetsuya Nakanishi, Kobe (JP)

(73) Assignees: KAWASAKI JUKOGYO KABUSHIKI KAISHA, Kobe (JP); MEDICAROID CORPORATION, Kobe (JP)

( * ) Notice: Subject to any disclaimer, the term of this patent is extended or adjusted under 35 U.S.C. 154(b) by 718 days.

(21) Appl. No.: 16/396,818

(22) Filed: Apr. 29, 2019

(65) Prior Publication Data

US 2019/0328471 A1  Oct. 31, 2019

(30) Foreign Application Priority Data

Apr. 27, 2018 (JP) .............................. JP2018-086895

(51) Int. Cl.
*A61B 34/37* (2016.01)
*A61B 1/00* (2006.01)
(Continued)

(52) U.S. Cl.
CPC .......... *A61B 34/37* (2016.02); *A61B 1/00006* (2013.01); *A61B 1/00045* (2013.01);
(Continued)

(58) Field of Classification Search
CPC . A61B 34/37; A61B 1/00006; A61B 1/00045; A61B 1/00149; A61B 1/0125;
(Continued)

(56) References Cited

U.S. PATENT DOCUMENTS

2008/0064921 A1* 3/2008 Larkin ................. A61B 1/0051
128/898
2009/0247821 A1* 10/2009 Rogers ............... A61B 1/00098
600/104
(Continued)

FOREIGN PATENT DOCUMENTS

JP   2015-024034 A   2/2015
JP   2015-150340 A   8/2015
(Continued)

*Primary Examiner* — Richard G Louis
(74) *Attorney, Agent, or Firm* — Oliff PLC

(57) ABSTRACT

A surgical system includes a robot main body, a slave controller, a display device that displays an endoscopic image, and an manipulation input device. The robot main body includes an entry guide having a plurality of guide bores, an entry guide support device that supports the entry guide, an instrument manipulator that has a surgical instrument provided at a distal end and is inserted into the entry guide, and an endoscope manipulator that has an endoscopic camera provided at a distal end and is inserted into the entry guide. The slave controller operates the robot main body such that the surgical instrument advances from an exit of the entry guide after the endoscopic camera advances from the exit of the entry guide and starts capturing in response to input of a body cavity insertion manipulation received by the manipulation input device.

20 Claims, 14 Drawing Sheets

(51) Int. Cl.
*A61B 1/313* (2006.01)
*A61B 1/05* (2006.01)
*A61B 17/34* (2006.01)
*A61B 34/00* (2016.01)
*A61B 34/30* (2016.01)
*A61B 17/00* (2006.01)

(52) U.S. Cl.
CPC ............ *A61B 1/00149* (2013.01); *A61B 1/05* (2013.01); *A61B 1/3132* (2013.01); *A61B 17/3423* (2013.01); *A61B 34/70* (2016.02); *A61B 2017/0034* (2013.01); *A61B 2017/3447* (2013.01); *A61B 2034/301* (2016.02); *A61B 2034/302* (2016.02)

(58) Field of Classification Search
CPC ..... A61B 1/05; A61B 1/3132; A61B 17/3423; A61B 34/70; A61B 17/29; A61B 2017/0034; A61B 2017/3447; A61B 2034/301; A61B 2034/302; A61B 2090/373; A61B 34/71; A61B 90/37; A61B 34/30; A61B 2017/00017; A61B 1/00154; A61B 1/0016; A61B 90/50; A61B 2017/003; A61B 2017/2908; A61B 2017/2938

See application file for complete search history.

(56) References Cited

U.S. PATENT DOCUMENTS

| | | |
|---|---|---|
| 2015/0230697 A1 | 8/2015 | Phee et al. |
| 2016/0135911 A1 | 5/2016 | Yanagihara et al. |
| 2016/0199138 A1 | 7/2016 | Cooper et al. |
| 2016/0339586 A1 | 11/2016 | Komuro et al. |

FOREIGN PATENT DOCUMENTS

| | | |
|---|---|---|
| JP | 2015-535702 A | 12/2015 |
| JP | 2016-530004 A | 9/2016 |

\* cited by examiner

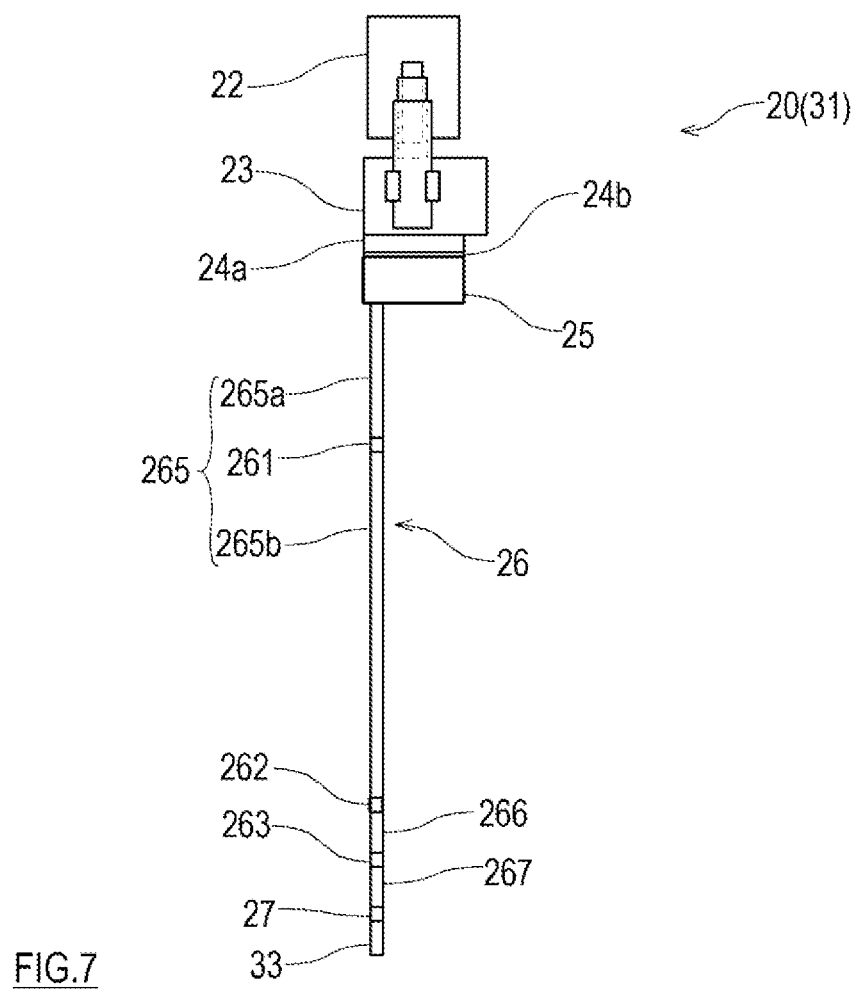

SURGICAL SYSTEM AND METHOD FOR CONTROLLING THE SAME

CROSS-REFERENCE TO RELATED APPLICATIONS

This application claims priority based on Japanese Patent Application No. 2018-086895 filed on Apr. 27, 2018, the entire disclosure of which is incorporated herein.

BACKGROUND OF THE INVENTION

(1) Field of the Invention

Conventionally, a surgical system including a master-slave type surgical assist robot has been known. In surgery using a surgical system, a surgeon remotely controls the operation of a surgical assist robot using a console, and the surgical assist robot performs surgery on a surgery site of a patient. For example, JP2016-530004A discloses this type of a surgical system.

A teleoperated surgical system described in JP2016-530004A is for performing single incision laparoscopic surgery. The teleoperated surgical system includes a patient cart (corresponding to a surgical assist robot) and a surgeon console. The patient cart includes a plurality of surgical device assemblies supported by a manipulator. The surgical device assembly includes an instrument including a surgical instrument and a movable wrist, a drive unit for the instrument, and a sterile adapter connecting them.

SUMMARY OF THE INVENTION

In single incision laparoscopic surgery, a plurality of surgical instruments and endoscopes are inserted into a single entry guide inserted into a body surface of the patient. A cross-sectional area of the entry guide is desirably small to reduce the burden on the patient, resulting in the concentration of surgical instruments and endoscopes at the entry and exit of the entry guide. Therefore, in the single incision laparoscopic surgery, a surgical tool is more difficult to manipulate than conventional multi-incision laparoscopic surgery due to the interference between the surgical instruments and the narrowing of the working space.

The present invention has been made in view of the circumstances described above, and an object of the present invention is to assist a surgeon in manipulating a surgical tool so as to avoid interference between the surgical instruments in a surgical system for single incision laparoscopic surgery.

A surgical system according to an aspect of the present embodiment includes a robot main body, a slave controller configured to control the robot main body, a display device configured to display an endoscopic image, and a manipulation input device configured to receive input from a surgeon and transmit a command corresponding to the input to the slave controller. The robot main body includes an entry guide having a plurality of guide bores, an entry guide support device that supports the entry guide, an instrument manipulator that has a surgical instrument at a distal end and is inserted into one of the guide bores of the entry guide, and an endoscope manipulator that has an endoscopic camera provided at a distal end and is inserted into another one of the guide bores of the entry guide. The manipulation input device includes a manipulation tool that receives input of a body cavity insertion manipulation. The slave controller operates the robot main body such that the surgical instrument advances from an exit of the entry guide after the endoscopic camera advances from the exit of the entry guide and starts capturing, in response to the input of the body cavity insertion manipulation.

Further, a method for controlling a surgical system according to an aspect of the present invention is a method for controlling a surgical system including a robot main body, a display device that displays an endoscopic image, and a manipulation input device that receives input from a surgeon. The robot main body includes: an entry guide having a plurality of guide bores; an entry guide support device that supports the entry guide; an instrument manipulator that has a surgical instrument provided at a distal end and is inserted into one of the guide bores of the entry guide; and an endoscope manipulator that has an endoscopic camera provided at a distal end and is inserted into another one of the guide bores of the entry guide. The method includes the steps of: receiving input of a body cavity insertion manipulation via the manipulation input device; causing the endoscopic camera to advance from an exit of the entry guide in response to the input of the body cavity insertion manipulation; causing the endoscopic camera to start capturing; and causing the surgical instrument to advance from the exit of the entry guide after the endoscopic camera starts capturing.

According to the surgical system and the method for controlling the surgical system, a surgeon can perform a manipulation for causing the surgical instrument to advance from the entry guide into a body cavity of a patient while checking an endoscopic image captured by the endoscopic camera. In this manner, it is possible to assist the surgeon in manipulating a surgical tool in such a manner as avoiding the interference between the surgical instruments and between the surgical instruments and a patient tissue.

The above object, other objects, features, and advantages of the present invention will be apparent from the following detailed description of the preferred implementation taken in conjunction with the accompanying drawings.

BRIEF DESCRIPTION OF THE DRAWINGS

FIG. 7 is a diagram showing an example of an endoscope manipulator having an endoscopic camera.

DETAILED DESCRIPTION OF PREFERRED EMBODIMENTS

Figure 1:
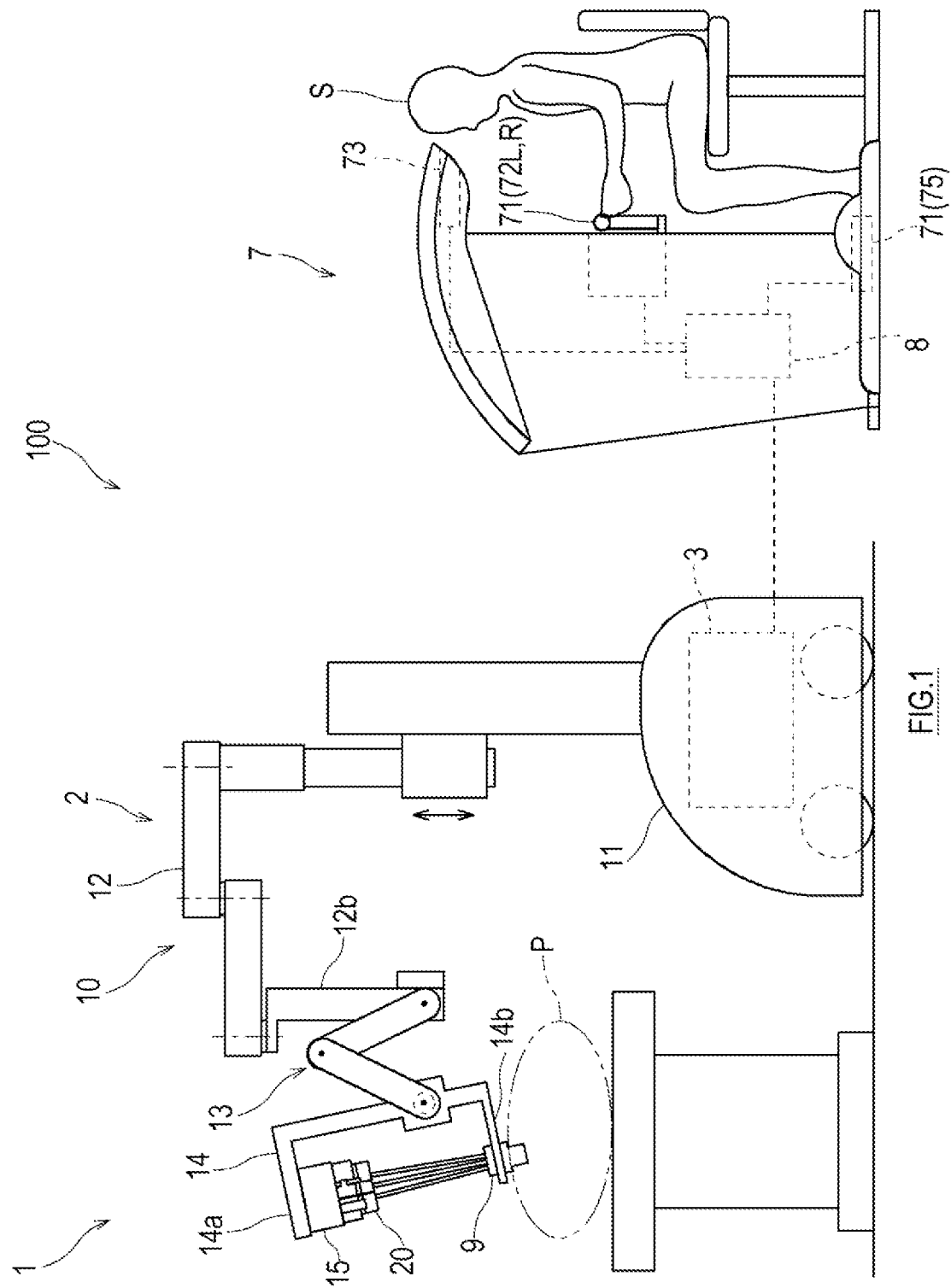
FIG. 1 is a diagram showing an overall schematic configuration of a surgical system according to an embodiment of the present invention.
Figure 2:
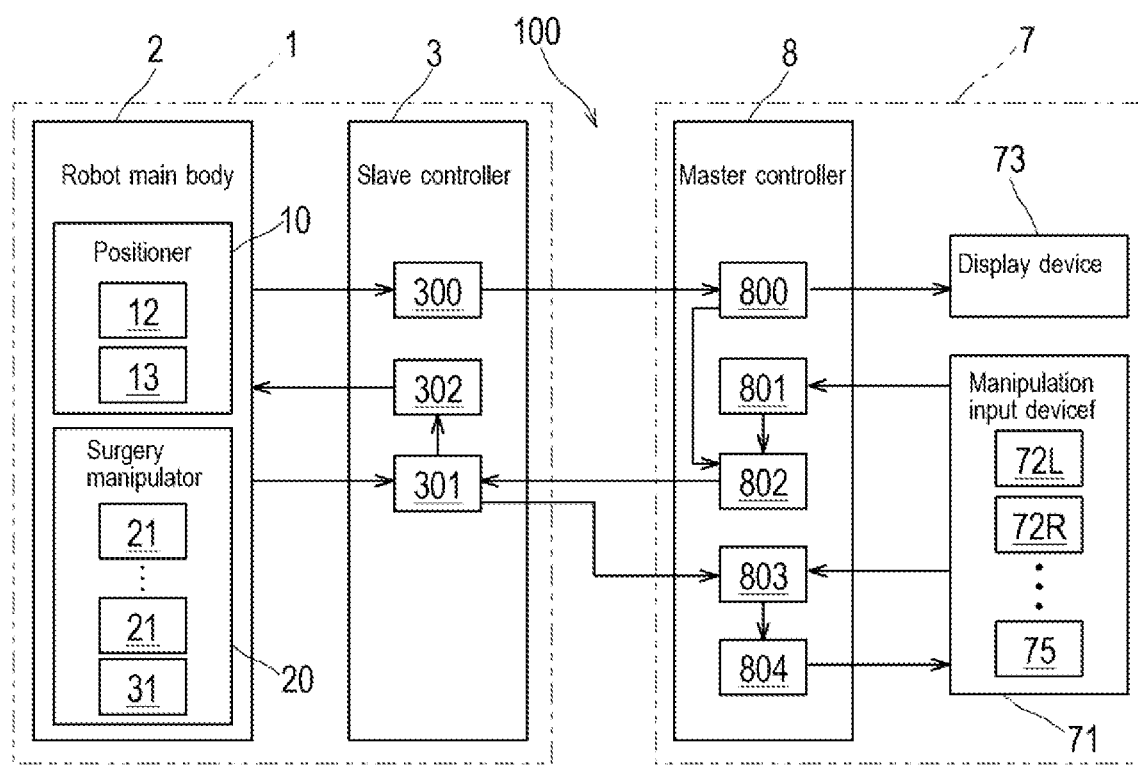
FIG. 2 is a block diagram showing a configuration of a control system of the surgical system.

Next, embodiments of the present invention will be described with reference to the drawings. FIG. 1 is a diagram showing an overall schematic configuration of a surgical system 100 according to an embodiment of the present invention, and FIG. 2 is a block diagram showing a control system of the surgical system 100. The surgical system 100 shown in FIGS. 1 and 2 is for performing single incision laparoscopic surgery, and includes a surgical assist robot 1 and a console 7. However, the surgical system 100 according to the present invention is not limited to the mode shown in FIGS. 1 and 2, and, for example, can be widely applied to a publicly-known surgical assist robot as disclosed in FIG. 2 of US2016/0199138A1 combined with a display device and a manipulation input device. Hereinafter, each constituent of the surgical system 100 according to the present embodiment will be described in detail.

[Surgical Assist Robot 1]

The surgical assist robot 1 constitutes an interface between the surgical system 100 and a patient P. The surgical assist robot 1 is placed beside the operating table on which the patient P lies in an operating room which is a sterile field.

The surgical assist robot 1 includes a robot main body 2 and a slave controller 3. The robot main body 2 includes a plurality of surgery manipulators 20, a single entry guide 9, and a positioner 10 for positioning the surgery manipulator 20 and the entry guide 9 on the patient P.

The entry guide 9 is attached to a cannula (not shown) placed on a body surface of the patient P. The entry guide 9 has a plurality of parallel guide bores 90 (see FIG. 8) extending in a predetermined insertion axial direction. The surgery manipulators 20 are individually inserted into the guide bores 90. The positioner 10 has a function as an entry guide support device for supporting the entry guide 9.

The positioner 10 includes a horizontal articulated manipulator 12 supported by a carriage 11, a support member 12b provided at a distal end of the horizontal articulated manipulator 12, a vertical articulated manipulator 13 supported by the horizontal articulated manipulator 12 via the support member 12b, and a support frame 14 provided at a distal end of the vertical articulated manipulator 13. However, the configuration of the positioner 10 is not limited to the present embodiment, and may be any configuration as long as the configuration allows the entry guide 9 to be positioned at a target position (including a posture) with excellent accuracy. The positioner 10 is described, for example, in JP-A-2017-104453, which is incorporated herein by reference.

The support frame 14 has a channel shape, and has one end and the other end facing each other with space therebetween. At one end of the support frame 14, an entry guide support portion 14b for supporting the entry guide 9 is provided. Further, at the other end of the support frame 14, a surgery manipulator support portion 14a is provided. Relative positions of the surgery manipulator support portion 14a and the entry guide support portion 14b may be variable or constant.

The surgery manipulator support portion 14a is provided with a support block 15 for collectively supporting the plurality of surgery manipulators 20. The plurality of the surgery manipulators 20 each include an instrument manipulator 21 having a surgical instrument 28 and an endoscope manipulator 31 having an endoscopic camera 33.

(Instrument Manipulator 21)

Figure 3:
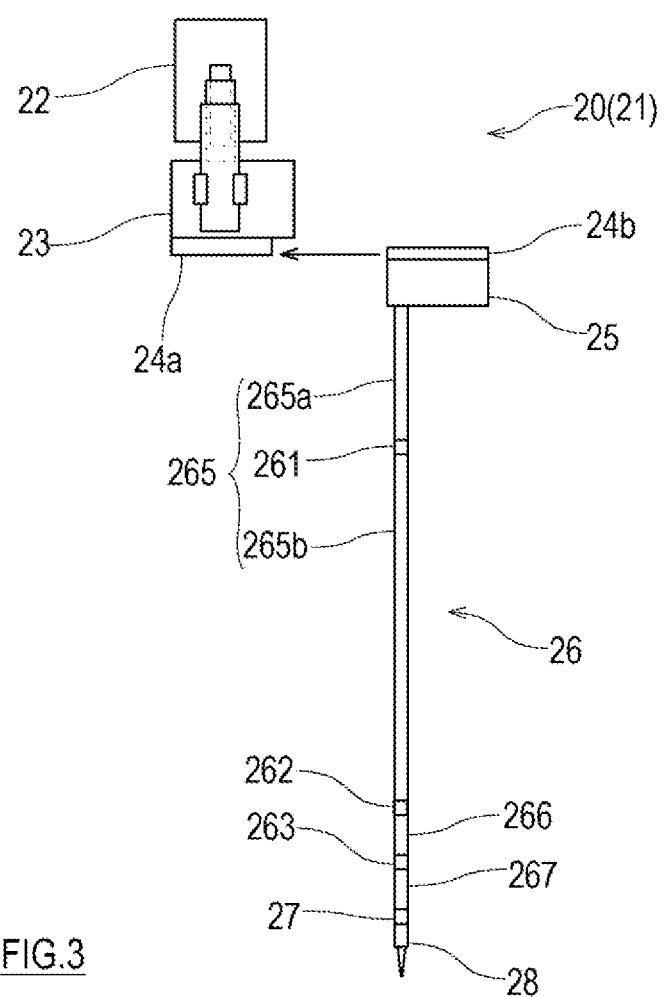
FIG. 3 is a diagram showing an example of an instrument manipulator having a surgical instrument.

FIG. 3 is a diagram showing an example of the instrument manipulator 21 having the surgical instrument 28. The instrument manipulator 21 shown in FIG. 3 includes a translation unit 22, a drive unit 23, a transmission unit 25, an elongated hollow shaft-like arm 26, a wrist 27, and the surgical instrument 28 as an end effector, which are connected in sequence from a proximal end toward a distal end. Note that the term "proximal" indicates that a distance along the robot main body 2 from the carriage 11 to a certain portion of the robot main body 2 is smaller than a distance along the robot main body 2 from the carriage 11 to another portion of the robot main body 2. Further, the term "distal" indicates that a distance along the robot main body 2 from the carriage 11 to a certain portion of the robot main body 2 is larger than a distance along the robot main body 2 from the carriage 11 to another portion of the robot main body 2. Note that, as for the surgery manipulator support portion 14a and the entry guide support portion 14b, it is assumed that the former is proximal with respect to the latter and the latter is distal with respect to the former.

The translation unit 22 forms a translational joint in the instrument manipulator 21. The translation unit 22 is what is called a linear motion device, and may be, for example, a motorized linear slide cylinder. The translation unit 22 is fixed to the support block 15. The drive unit 23 is attached to a slider of the translation unit 22. The transmission unit 25, the arm 26, the wrist 27, and the surgical instrument 28 are integrally configured, and the transmission unit 25 is detachably connected to the drive unit 23 with adapters 24a and 24b interposed therebetween. A ball screw with a motor, rack and pinion with a motor, or a linear motor may be employed as the translation unit 22, in addition to the motorized linear slide cylinder.

The operation of the translation unit 22 causes portions of the instrument manipulator 21 other than the translation unit 22 to move in parallel with an insertion axial direction of the entry guide 9. By such a translational movement of the instrument manipulator 21, a distal portion including the arm 26 of the instrument manipulator 21, the wrist 27 and the surgical instrument 28 can be inserted into the guide bore 90 of the entry guide 9, and a distal portion of the instrument manipulator 21 inserted into the guide bore 90 can be caused to advance into or be retracted from a body cavity of the patient P.

Figure 4A:
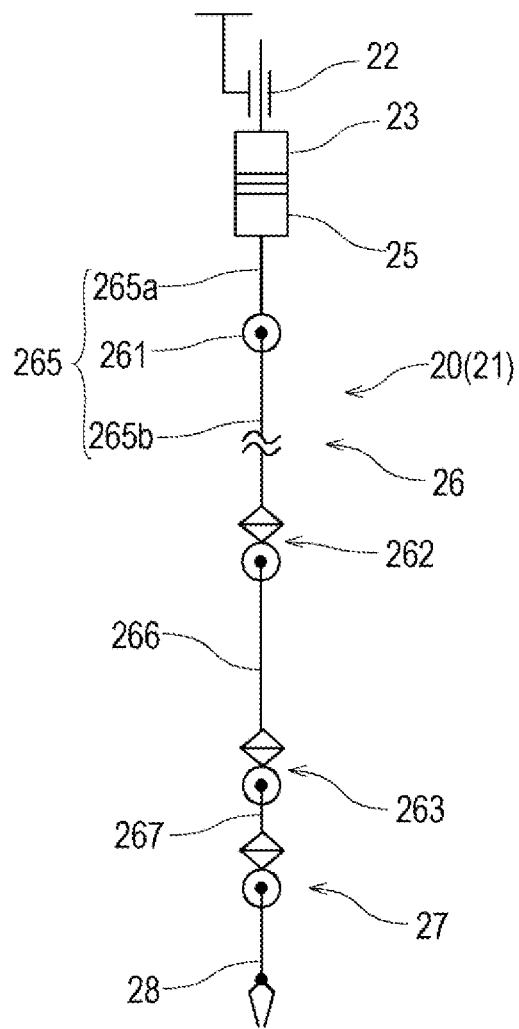
FIG. 4A is a diagram for describing an axial configuration of the instrument manipulator, and is a diagram of the instrument manipulator having a six-axis arm.
Figure 4B:
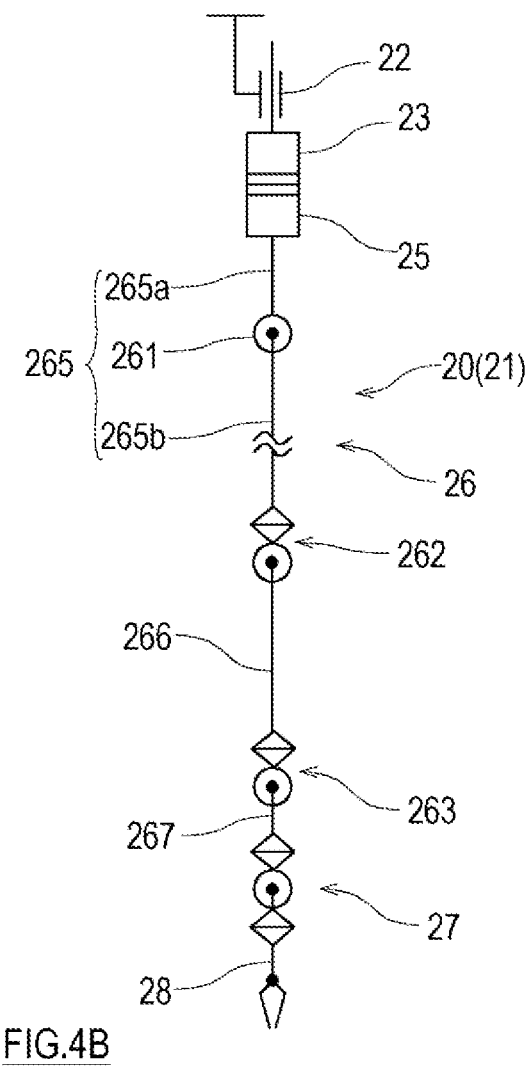
FIG. 4B is a diagram for describing an axial configuration of the instrument manipulator, and is a diagram of the instrument manipulator having a seven-axis arm.

The arm 26 includes a proximal link 265, a middle link 266, and a distal link 267 connected in sequence. These links are comprised of a hollow straight pipe. As shown in FIG. 4A, the proximal link 265 and the middle link 266 are connected by a shoulder 262 including a twisting joint and a bending joint. The middle link 266 and the distal link 267 are connected by an elbow 263 including a bending joint. However, as shown in FIG. 4B, the elbow 263 may include a bending joint and a twisting joint.

Figure 5A:
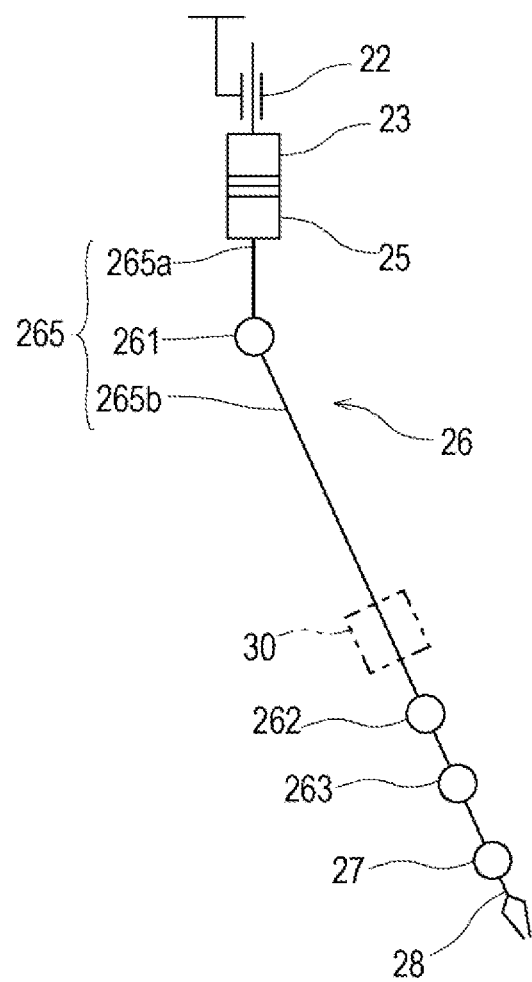
FIG. 5A is a diagram for describing a position of an auxiliary joint of the instrument manipulator, showing the instrument manipulator in which the auxiliary joint is closer to the proximal side than to an entry guide.
Figure 5B:
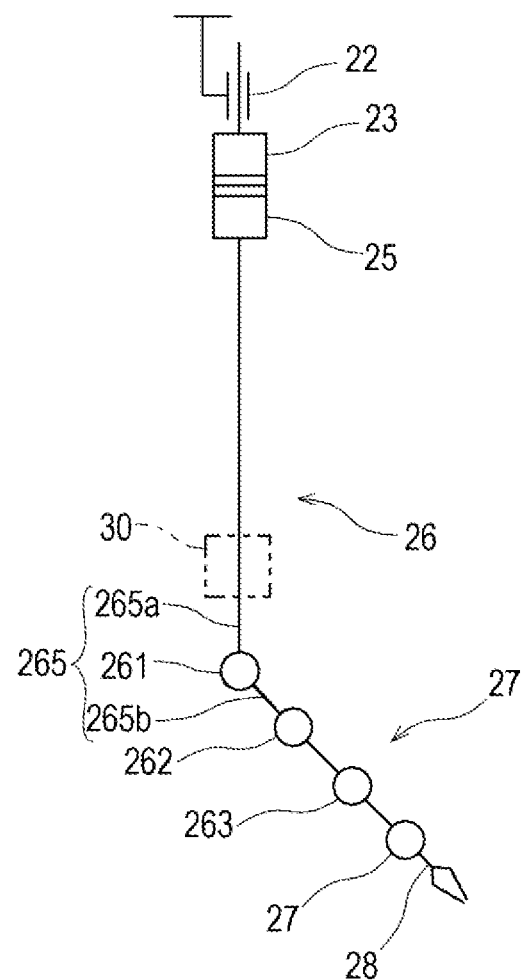
FIG. 5B is a diagram for describing a position of the auxiliary joint of the instrument manipulator, showing the instrument manipulator in which the auxiliary joint is closer to the distal side than to the entry guide.

The proximal link 265 may include a first proximal link 265a, a second proximal link 265b, and an auxiliary joint 261 that bendably and rotatably connects the first proximal link 265a and the second proximal link 265b. As shown in FIG. 5A, the auxiliary joint 261 may be provided at a proximal portion of the arm 26 which is not inserted into the entry guide 9. Alternatively, as shown in FIG. 5B, the auxiliary joint 261 may be provided at a distal portion of the arm 26 which advances from an exit of the entry guide 9 to a body cavity. The auxiliary joint 261 has its movement fixed during surgery after the instrument manipulator 21 is inserted into a body cavity. Fixing of the movement of the auxiliary joint 261 is performed by use of a brake or control for maintaining the posture of the auxiliary joint 261.

Returning to FIG. 3, a distal end of the arm 26 is connected to a proximal end of the wrist 27. The distal end of the wrist 27 is connected to the proximal end of the surgical instrument 28. As shown in FIG. 4A, the wrist 27 includes a bending joint and a twisting joint that are connected in sequence from a distal side.

The elbow 263 and the shoulder 262 may interlock such that the proximal link 265 (second proximal link 265b) and the distal link 267 remain parallel. A mechanism for interlocking the elbow 263 and the shoulder 262 is described in US 2017/056118 A1, which is incorporated herein by reference. Alternatively, the elbow 263 and the shoulder 262 may operate independently, causing the proximal link 265 and the distal link 267 to be non-parallel.

The bending joints included in the arm 26 and the wrist 27 may be obtained by, for example, a plurality of plate-shaped segments arranged in series in a thickness direction and a manipulation cable inserted in the thickness direction across the plurality of segments. Such a bending joint is described, for example, in International Publication WO2017/006373 A1, which is hereby incorporated by reference. However, the bending joint included in the arm 26 and the wrist 27 is not limited to the above configuration, and a publicly-known bending joint structure may be employed.

The twisting joint included in the arm 26 and the wrist 27 may be obtained by, for example, an inner and outer double cylinder and a manipulation cable for rotating the inner cylinder with respect to the outer cylinder. Such a twisting joint is described, for example, in International Publication WO2017/006374 A1, which is hereby incorporated by reference. However, the twisting joint included in the arm 26 and the wrist 27 is not limited to the above configuration, and a publicly-known twisting joint structure may be employed.

Figure 6A:
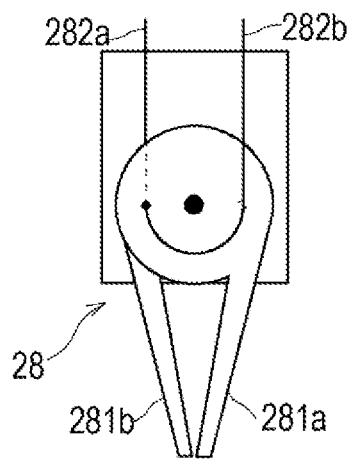
FIG. 6A is a diagram for describing transformation of a forceps which is an example of a surgical instrument, showing the forceps in a state of gripping an object.
Figure 6B:
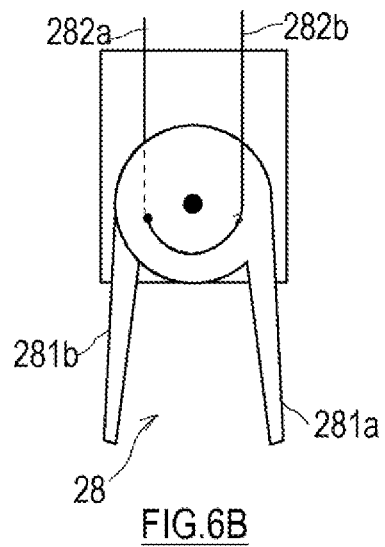
FIG. 6B is a diagram for describing transformation of the forceps which is an example of a surgical instrument, showing the forceps in a state after releasing the gripped object.
Figure 6C:
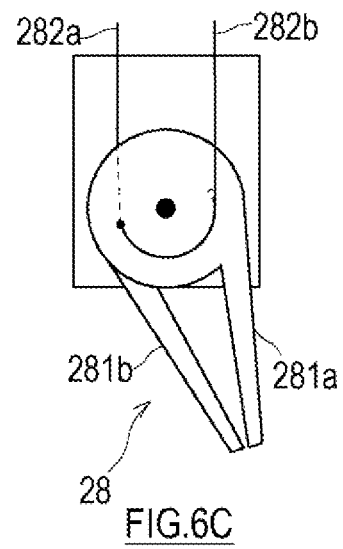
FIG. 6C is a diagram for describing transformation of the forceps which is an example of a surgical instrument, showing the forceps in a state after being moved without releasing the gripped object.

The surgical instrument 28 means an actual manipulated part which is inserted at a surgical site in the abdominal cavity of the patient P and can be driven from the outside of the abdominal cavity to perform desired treatment or a medical function of a target tissue at the surgical site. The surgical instrument 28 illustrated in each of FIGS. 6A to 6C includes a pair of jaws 281a and 281b. Each of the jaws 281a and 281b has an independent drive system and operates independently. For example, independent manipulation cables 282a and 282b are connected to the jaws 281a and 281b. In the surgical instrument 28 including such the pair of jaws 281a and 281b, as shown in FIG. 6A, the jaws 281a and 281b can be rotated in opposite directions such that distal ends of the jaws 281a and 281b approach each other, thereby gripping an object. From the state of gripping the object (FIG. 6A), the jaws 281a and 281b can be rotated in opposite directions such that the distal ends of the jaws 281a and 281b are separated from each other as shown in FIG. 6B, thereby releasing the gripped object. Further, as shown in FIG. 6C, the jaws 281a and 281b can be rotated in the same direction from the state of gripping the object (FIG. 6A), thereby moving the gripped object without moving the arm 26 and the wrist 27. However, the surgical instrument 28 is not limited to the above configuration. For example, the pair of jaws 281a and 281b of the surgical instrument 28 may be configured to interlock by one drive system. For the description of the drive system in this case, JP-A-2009-254761 is incorporated herein by reference.

The surgical instrument 28 may be a surgical instrument, such as a forceps, a grasper, scissors, a stapler, a needle holder, an electrosurgical knife, and the like. Further, the surgical instrument 28 may also be an electrically driven device, such as an electrosurgical electrode, a transducer, a sensor, or the like. Further, the surgical instrument 28 may be a nozzle for supplying fluid for suction, gas injection, cleaning, a treatment fluid, accessory introduction, biopsy and removal, and the like.

The wrist 27 and the arm 26 are hollow, and manipulation cables and various cables of the surgical instrument 28, the wrist 27, and the arm 26 extend through the wrist 27 and the arm 26 to the transmission unit 25. The transmission unit 25 is provided with a drive disk (not shown) in which a manipulation cable is wound around each manipulation cable. Torque is transmitted to each drive disk from a drive source (not shown) such as a servomotor provided in the drive unit 23 via the adapters 24a and 24b. The manipulation cable is loosened or pulled by the rotation of the drive disk, so that the surgical instrument 28, the wrist 27, and the arm 26 operate.

(Endoscope Manipulator 31)

FIG. 7 is a diagram showing an example of the endoscope manipulator 31 having an endoscopic camera 33. The endoscope manipulator 31 shown in FIG. 7 is provided with the endoscopic camera 33 including an objective lens and a light guide at a distal end.

The endoscope manipulator 31 has a substantially similar configuration as the instrument manipulator 21 except for the surgical instrument 28 provided at the distal end. That is, in the above description of the instrument manipulator 21, the configuration of the endoscope manipulator 31 can be described by replacing the surgical instrument 28 provided at the distal end with the endoscopic camera 33. From the above, detailed description of the configuration of the endoscope manipulator 31 including the endoscopic camera 33 will be omitted by referring to the description of the instrument manipulator 21 described above. Note that the surgical assist robot 1 according to the present embodiment has an axial structure in which the endoscope manipulator 31 and the instrument manipulator 21 are similar. However, the endoscope manipulator 31 has an axial structure different from that of the instrument manipulator 21.

(Slave Controller 3)

The slave controller 3 is communicably connected to the console 7. The slave controller 3 receives a command corresponding to the input received by the console 7 and operates the robot main body 2 of the surgical assist robot 1 based on the command. Further, the slave controller 3 transmits information to the console 7 so as to cause the console 7 to display an endoscope image of the endoscopic camera 33 or cause the console 7 to perform operation corresponding to operation of the robot main body 2.

The slave controller 3 is what is called a computer, and includes an arithmetic processing unit, such as a CPU, and a storage unit, such as a ROM and a RAM (all not shown). The storage unit stores a program executed by the arithmetic processing unit, various pieces of fixed data, and the like. The arithmetic processing unit performs data transmission and reception with other devices including the console 7. Further, the arithmetic processing unit performs input of detection signals from various sensors and output of control signals to each control target. In the slave controller 3, the arithmetic processing unit reads and executes software, such as a program, stored in the storage unit to perform processing for performing a function as the slave controller 3 described later. Note that the slave controller 3 may execute each processing by centralized control by a single computer, or may execute each processing by distributed control by cooperation of a plurality of computers. Further, the slave controller 3 may be configured with a microcontroller, a programmable logic controller (PLC), or the like.

The slave controller 3 has a positioner control function for controlling operation of the positioner 10 so as to position the entry guide 9 at a predetermined position and in a predetermined posture. The horizontal articulated manipulator 12 and the vertical articulated manipulator 13 of the positioner 10 include a servomotor provided for each joint, a rotation sensor for detecting a rotational position of each joint, and a drive unit including a power transmission mechanism for transmitting power of the servomotor to a joint (all not shown).

The slave controller 3 has a surgical instrument control function for controlling operation of each of the instrument manipulators 21. More specifically, the slave controller 3 has a function of controlling operation of the surgical instrument 28 and a function of controlling operation of the instrument manipulator 21 so as to bring the surgical instrument 28 into a position and a posture corresponding to a command. Each of the instrument manipulators 21 include a servomotor provided for each joint, a rotation sensor for detecting a rotational position of a motor, and a drive unit including a power transmission mechanism for transmitting power of the servomotor to a joint (all not shown).

The slave controller 3 has an endoscope control function for controlling operation of the endoscope manipulator 31. More specifically, the slave controller 3 has a function of controlling operation of the endoscopic camera 33 and a function of controlling operation of the endoscope manipulator 31 so as to bring the endoscopic camera 33 into a position and a posture corresponding to a command. The endoscope manipulator 31 includes a servomotor provided for each joint, a rotation sensor for detecting a rotational position of a motor, and a drive unit including a power transmission mechanism for transmitting power of the servomotor to a joint (all not shown).

[Console 7]

The console 7 constitutes an interface between the surgical system 100 and a surgeon S, and is a device for manipulating the surgical assist robot 1. The console 7 is installed beside an operating table or away from the operating table in an operating room or outside the operating room.

The console 7 includes a manipulation input device 71 for receiving an input from the surgeon S, a display device 73 for displaying an image captured by the endoscopic camera 33, and a master controller 8. The manipulation input device 71 includes a pair of left and right master manipulators 72L and 72R, and a manipulation pedal 75. Similar to the slave controller 3, the master controller 8 may be configured with a computer and the like. The console 7 is described, for example, in JP-A-2017-189495, which is incorporated herein by reference.

The pair of left and right master manipulators 72L and 72R are provided with a manipulation unit at each distal end, and the surgeon S applies a manipulation force to the manipulation unit. In the present embodiment, the pair of left and right master manipulators 72L and 72R are manipulation tools that receive input of a movement manipulation for a position and a posture of the endoscopic camera 33 and the surgical instrument 28. Further, the manipulation pedal 75 is a manipulation tool that receives input of manipulations, such as zooming the endoscopic camera 33, switching control modes, and switching the instrument manipulator 21 associated with the pair of left and right master manipulators 72L and 72R. The manipulation input device 71 further includes a manipulation tool that receives an input of a body cavity insertion manipulation of the surgical instrument 28, a manipulation tool that receives an input of a manipulator return manipulation, and the like. One of the master manipulators 72L and 72R and the manipulation pedal 75 may be used as these manipulation tools, or publicly-known manipulation tools, such as a lever, a button, a touch panel, a joystick, a motion capture, and the like, may be provided. The manipulation input device 71 may have a drive mechanism (not shown) for applying a reaction force to a manipulation force of the surgeon S to the manipulation unit.

The surgeon S inputs manipulations regarding the movement of the end effector provided at a distal end of the slave manipulator by directly moving the manipulation unit of the master manipulators 72L and 72R while checking an affected area on the endoscopic image displayed on the display device 73. The slave manipulator is, for example, the instrument manipulator 21 or the endoscope manipulator 31 associated with the master manipulators 72L and 72R by manipulation of the manipulation pedal 75, and the end effector is the surgical instrument 28 or the endoscopic camera 33.

The master controller 8 includes an image processing unit 800, an input processing unit 801, a movement command generation unit 802, a master position command generation unit 803, and a master driver 804. The input processing unit 801 obtains a rotation angle of each joint from the rotation sensor provided corresponding to each joint of the master manipulators 72L and 72R, and obtains a position and a speed (moving speed) of the manipulation unit from the rotation angle of each joint. The movement command generation unit 802 generates a movement command including a position and a speed for the slave manipulator based on the position and the speed of the manipulation unit acquired from the input processing unit 801. The generated movement command is transmitted to the slave controller 3.

The slave controller 3 includes an image acquisition unit 300, a slave position command generation unit 301, and a slave driver 302. The image acquisition unit 300 acquires image data captured by the endoscopic camera 33 and transmits the image data to the image processing unit 800 of the master controller 8. The slave position command generation unit 301 generates a slave position command from a movement command acquired from the movement command generation unit 802. To the slave position command, restriction of a movement range, restriction of a movement speed, or the like set in advance may be applied. The slave driver 302 obtains a position of each joint from the rotation sensor provided corresponding to each joint of the slave manipulator, obtains driving torque of each joint from the slave position command and each joint position, and supplies a current corresponding to the driving torque to the servomotor that drives a corresponding joint. As a result, the slave manipulator operates in response to the movement of the manipulation unit of the master manipulators 72L and 72R.

On the other hand, the slave position command generated by the slave position command generation unit 301 is transmitted to the master position command generation unit 803 of the master controller 8. Based on the acquired slave position command and the movement command which is acquired from the movement command generation unit 802, the master position command generation unit 803 generates a master position command such that the manipulation unit of the master manipulators 72L and 72R is at the position and in the posture each corresponding to the end effector of the slave manipulator. The master position command includes a reaction force described later. The master driver 804 obtains a drive torque of each joint from the master position command and each joint position of the master manipulators 72L and 72R, and supplies a current corresponding to the drive torque to a corresponding joint motor. As a result, the position and the posture of the manipulation unit of the master manipulators 72L and 72R operate in a manner corresponding to the position and the posture of the end effector of the slave manipulator.

[Operation Example of the Surgical System 100]

In the surgical system 100 configured as described above, the command corresponding to the input received by the console 7 is input to the slave controller 3. The slave controller 3 operates the robot main body 2 in a manner, for example, described below in response to the input received by the console 7.

(Positioning Operation of the Entry Guide 9)

In response to input of a positioning manipulation of the entry guide 9 received by the console 7, the slave controller 3 operates the positioner 10 so as to position the entry guide 9 at a predetermined position and in a predetermined posture with respect to a cannula placed on a body surface of the patient P. When the entry guide 9 is positioned, the plurality of surgery manipulators 20 are also automatically positioned.

(Body Cavity Insertion Operation of the Surgical Instrument 28)

In response to input of a body cavity insertion manipulation of the surgical instrument 28 received by the console 7, the slave controller 3 operates each of the translation units 22 such that the endoscopic camera 33 and the surgical instrument 28 are inserted into a body cavity. The slave controller 3 starts capturing by the endoscopic camera 33 at a predetermined timing at which the endoscopic camera 33 is inserted into the body cavity.

Figure 8A:
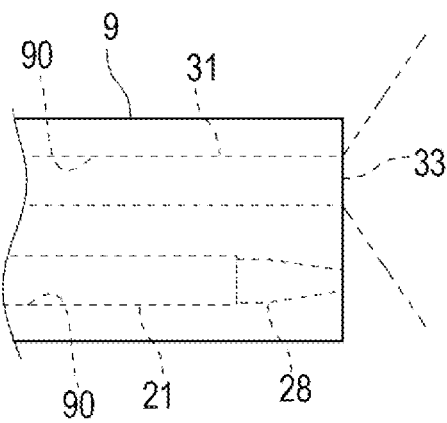
FIG. 8A is a diagram for describing how the instrument manipulator and the endoscope manipulator advance from the entry guide to a body cavity, showing a state before the instrument manipulator and the endoscope manipulator advance from the entry guide.
Figure 8B:
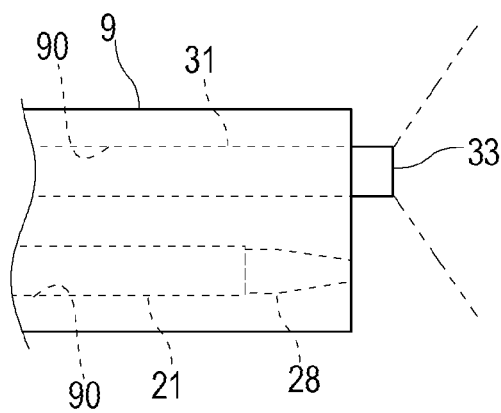
FIG. 8B is a diagram for describing how the instrument manipulator and the endoscope manipulator advance from the entry guide to the body cavity, showing a state in which the endoscope manipulator starts to advance from the entry guide.
Figure 8C:
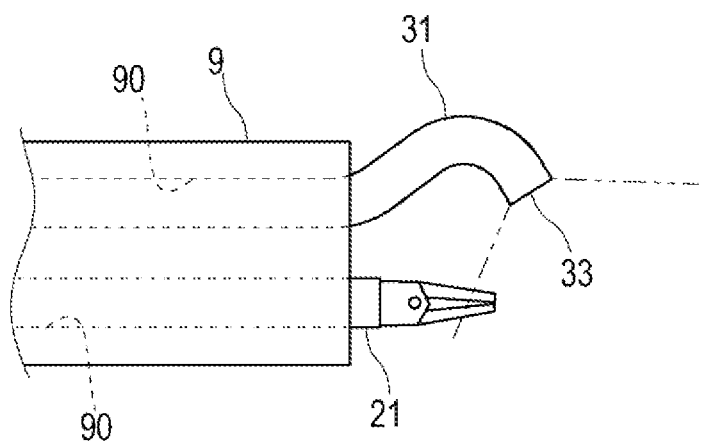
FIG. 8C is a diagram for describing how the instrument manipulator and the endoscope manipulator advance from the entry guide to a body cavity, showing a state in which the instrument manipulator starts to advance from the entry guide.

Here, with reference to FIGS. 8A to 8C, operation of the robot main body 2 when the endoscopic camera 33 and the surgical instrument 28 are caused to advance into a body cavity will be described. Each of FIGS. 8A to 8C is a diagram describing a state in which the instrument manipulator 21 and the endoscope manipulator 31 advance from the entry guide 9 to a body cavity. FIG. 8A is a diagram showing a state before the instrument manipulator 21 and the endoscope manipulator 31 advance from the entry guide 9. FIG. 8B shows a state in which the endoscope manipulator 31 has started advancing from the entry guide 9. FIG. 8C shows a state in which the instrument manipulator 21 has started advancing from the entry guide 9.

As shown in FIG. 8A, the instrument manipulator 21 and the endoscope manipulator 31 before advancing to a body cavity stand by in different ones of the guide bores 90 of the entry guide 9.

As shown in FIG. 8B, the endoscopic camera 33 advances from an exit of the entry guide 9 into the body cavity prior to the surgical instrument 28. A timing at which capturing by the endoscopic camera 33 starts is, for example, when the endoscopic camera 33 is in the entry guide 9 (FIG. 8A). Further, for example, a timing at which capturing by the endoscopic camera 33 starts is when the endoscopic camera 33 starts advancing from the entry guide 9 (FIG. 8B). In other words, in response to the start of capturing by the endoscopic camera 33, the surgical instrument 28 advances from the exit of the entry guide 9. Here, since a relative positional relationship between the translation unit 22 and the entry guide 9 is known, the slave controller 3 can obtain a position of the endoscope manipulator 31 relative to the entry guide 9 based on a displacement amount of the endoscope manipulator 31 in an insertion and removal direction by the translation unit 22.

As described above, after the endoscopic camera 33 starts capturing, the surgical instrument 28 provided at a distal end of the instrument manipulator 21 advances from the exit of the entry guide 9 into the body cavity, as shown in FIG. 8C. Here, since a relative positional relationship between the translation unit 22 and the entry guide 9 is known, the slave controller 3 can obtain a position of the instrument manipulator 21 relative to the entry guide 9 based on a displacement amount of the instrument manipulator 21 in an insertion and removal direction by the translation unit 22.

The slave controller 3 controls operation of the instrument manipulator 21 so as to maintain a linear shape of a portion of the instrument manipulator 21 advancing from the exit of the entry guide 9 into the body cavity after the surgical instrument 28 advances into the body cavity until the surgical instrument 28 enters a field of view of the endoscopic camera 33. Here, the slave controller 3 (or the master controller 8) determines that the surgical instrument 28 has entered the field of view of the endoscopic camera 33 based on the position and posture information of the surgical instrument 28 and the endoscopic camera 33, and the information on the field of view of the endoscopic camera 33. The slave controller 3 (or the master controller 8) may determine that the surgical instrument 28 has entered the field of view of the endoscopic camera 33 by analyzing an endoscopic image captured by the endoscopic camera 33, and recognizing the surgical instrument 28 shown on the endoscopic image.

Figure 9:
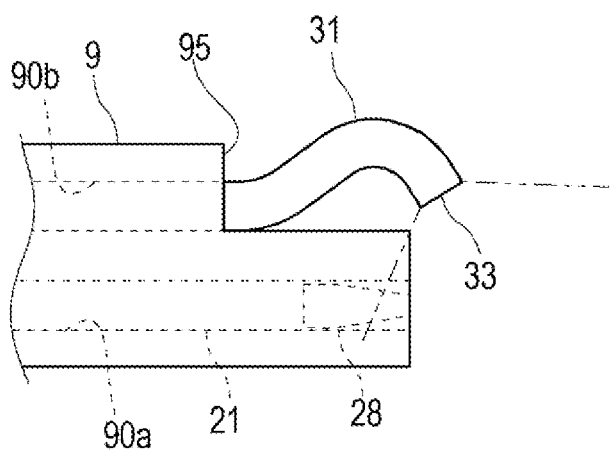
FIG. 9 is a diagram showing a variation of the entry guide.

In order to put the surgical instrument 28, which starts advancing into the body cavity from the exit of the entry guide 9, in the field of view of the endoscopic camera 33, the distal end portion of the guide bore 90 into which the endoscope manipulator 31 is inserted may be positioned closer to the proximal side of the entry guide 9 than the distal end of the guide bore 90 into which the instrument manipulator 21 is inserted in the entry guide 9. FIG. 9 is a diagram showing a variation of the entry guide 9. In the entry guide 9 shown in FIG. 9, part of the distal end of the entry guide 9 is cut out. In this manner, the distal end of the guide bore 90b into which the endoscope manipulator 31 is inserted is positioned closer to the proximal side of the entry guide 9 than the distal end of the guide bore 90a into which the instrument manipulator 21 is inserted. In this manner, an exit 95 of the entry guide 9 of the endoscope manipulator 31 is positioned closer to the proximal side in the entry guide 9 than an exit of the entry guide 9 of the instrument manipulator 21. In this manner, the wrist 27 of the endoscope manipulator 31 that has advanced from the exit 95 of the entry guide 9 can be moved to put the exit of the entry guide 9 of the instrument manipulator 21 in the field of view of the endoscopic camera 33. Then, the surgical instrument 28 starting to advance into the body cavity from the exit of the entry guide 9 is in a state of being in the field of view of the endoscopic camera 33, and, while the state is maintained, the surgical instrument 28 advances from the exit of the entry guide 9 to the body cavity. In this manner, it is possible to perform manipulation by checking the surgical instrument 28 in an endoscopic image from a time point at which the surgical instrument 28 starts to advance into the body cavity.

(Surgery Operation of the Surgical Instrument 28)

The slave controller 3 receives the command corresponding to the input received by the console 7 and operates the instrument manipulator 21 to change the position and posture of the surgical instrument 28 inserted into the body cavity based on the command.

Since the plurality of instrument manipulators 21 are inserted in the single entry guide 9, each of the instrument manipulators 21 is operated such that, in principle, the elbow 263 is moved radially outward in a cross section of the entry guide 9.

Figure 10:
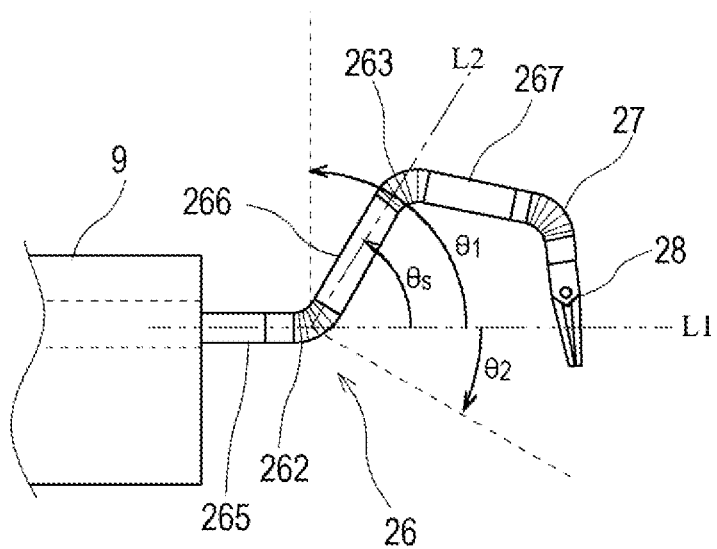
FIG. 10 is a diagram for describing a movable range of a shoulder of the instrument manipulator.

FIG. 10 is a diagram for describing a movable range θs of the shoulder 262 of the instrument manipulator 21. As shown in FIG. 10, an extension of a center line L1 of the proximal link 265 connected to the proximal end of the shoulder 262 is defined at 0 degrees. The center line L1 of the proximal link 265 passes through the center of a cross section of the proximal link 265 and is a straight line parallel to a longitudinal direction of the proximal link 265. The slave controller 3 restricts the movable range θs of the shoulder 262 to a range (θ1) of rotating a center line L2 of the middle link 266 connected to the distal end of the shoulder 262 toward an outer peripheral side of the entry guide 9 by 0 degrees or more and less than 90 degrees, more preferably, by 0 degrees or more and less than 50 degrees, and a range (θ2) of rotating the center line L2 of the middle link 266 toward an inner peripheral side of the entry guide 9 by 0 degrees or more and less than 30 degrees. The center line of the middle link 266 passes through the center of a cross section of the middle link 266 and is a straight line parallel to a longitudinal direction of the middle link 266. Note that, "toward an outer peripheral side of the entry guide 9" means a direction toward the outer peripheral side of the entry guide 9 as viewed from the guide bore 90 in which the instrument manipulator 21 is inserted. Similarly, "toward an inner peripheral side of the entry guide 9" means a direction toward the inner peripheral side of the entry guide 9 as viewed from the guide bore 90 in which the instrument manipulator 21 is inserted. As described above, in a case where the middle link 266 is rotated with respect to the proximal link 265 from a state in which the longitudinal direction of the proximal link 265 and the longitudinal direction of the middle link 266 are parallel, a movable range to one side is made smaller than a movable range to the other side. More specifically, in a case where the middle link 266 is rotated with respect to the proximal link 265 from a state in which the longitudinal direction of the proximal link 265 and the longitudinal direction of the middle link 266 are parallel, a movable range to the inner peripheral side of the entry guide 9 is made smaller than a movable range to the outer peripheral side of the entry guide 9.

Figure 11:
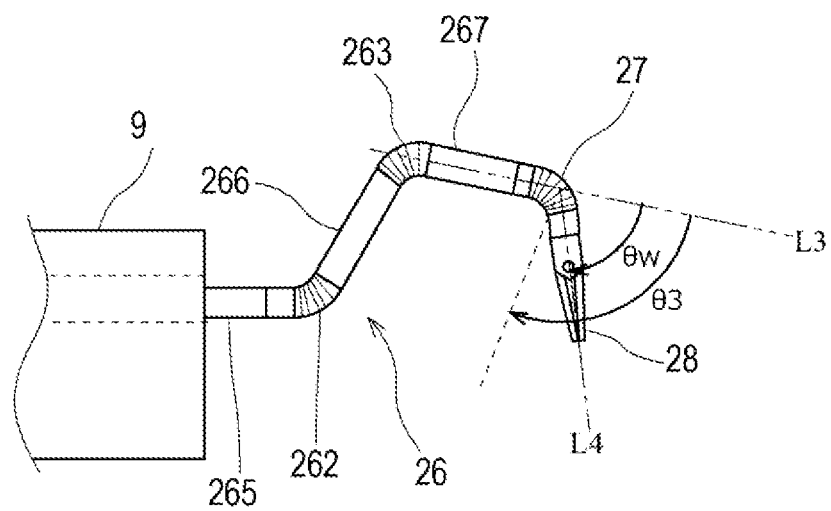
FIG. 11 is a diagram for describing a movable range of a wrist of the instrument manipulator.

FIG. 11 is a diagram for describing a movable range θw of the wrist 27 of the instrument manipulator 21. As shown in FIG. 11, an extension of a center line L3 of the distal link 267 connected to the proximal end of the wrist 27 is defined at 0 degrees. The center line L3 of the distal link 267 passes through the center of a cross section of the distal link 267 and is a straight line parallel to a longitudinal direction of the distal link 267. The slave controller 3 restricts the movable range θw of the wrist 27 to a range (θ3) of rotating a center line L4 of the surgical instrument 28 toward the inner peripheral side of the entry guide 9 by 0 degrees or more and less than 100 degrees, more preferably, by 0 degrees or more and less than 90 degrees. The center line L4 of the surgical instrument 28 is a straight line passing through the proximal end and the distal end of the surgical instrument 28. As described above, in a case where the surgical instrument 28 is rotated with respect to the distal link 267 from a state in which the longitudinal direction of the distal link 267 and the center line of the surgical instrument 28 are parallel, a movable range to one side is made smaller than a movable range to the other side. More specifically, in a case where the surgical instrument 28 is rotated with respect to the distal link 267 from a state in which the longitudinal direction of the distal link 267 and the center line of the surgical instrument 28 are parallel, a movable range to the inner peripheral side of the entry guide 9 is made larger than a movable range to the outer peripheral side of the entry guide 9.

When operating the instrument manipulator 21 based on a movement command, the slave controller 3 restricts an overhang amount W of the instrument manipulator 21 in addition to restricting the movable range of the wrist 27 and the shoulder 262 as described above.

Figure 12:
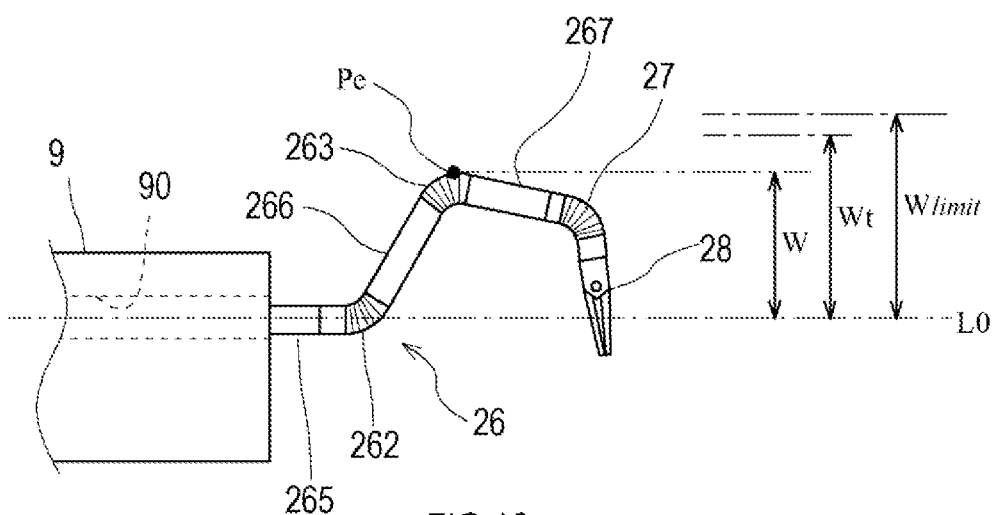
FIG. 12 is a diagram for describing the amount of overhang of the instrument manipulator.

FIG. 12 is a diagram for describing the overhang amount W of the instrument manipulator 21. As shown in FIG. 12, in a portion of the instrument manipulator 21 advancing from the exit of the entry guide 9 to the body cavity, a point that is most distant from a center line L0 of the guide bore 90 through which the instrument manipulator 21 is inserted toward a radially outer side of the guide bore 90 is referred to as an "outermost point Pe". Then, a distance from the center line L0 of the guide bore 90 to the outermost point Pe is referred to as an "overhang amount W". The slave controller 3 can obtain the overhang amount W of the instrument manipulator 21 based on a manipulation amount of the manipulation cable by the drive unit 23. A point that is most distant to a radially outer side in a cross section of the guide bore 90 from the center line L0 of the guide bore 90 in which the instrument manipulator 21 is inserted on the elbow 263 of the instrument manipulator 21 may be the "outermost point Pe". The elbow 263 often enters a blind spot of the endoscopic camera 33.

The slave controller 3 compares the overhang amount W obtained by calculation with a predetermined overhang amount threshold Wt stored in advance, and performs predetermined processing when the overhang amount W exceeds the overhang amount threshold Wt. The overhang amount threshold Wt is smaller than a limit value Wlimit. The predetermined processing performed by the slave controller 3 includes at least one of processing of outputting a warning to the console 7, processing of temporarily stopping the operation of the robot main body 2, processing of reducing a ratio (scale) of a displacement amount of the instrument manipulator 21 corresponding to the manipulation amount received by the console 7, and processing of outputting information to the console 7 such that a reaction force is applied to a manipulation force which is a manipulation force that is received by the manipulation input device 71 and increases the overhang amount W. In a case of temporarily stopping the operation of the robot main body 2, the slave controller 3 resumes the operation of the robot main body 2, which has been stopped, in response to input of a stop release manipulation received by the console 7.

In the above, the slave controller 3 can further time-differentiate the overhang amount W to obtain a change amount (overhang change amount ΔW) per unit time of the overhang amount W. The slave controller 3 stores a predetermined correspondence relationship in which the overhang amount threshold Wt decreases as the overhang change amount ΔW increases. Then, the slave controller 3 may obtain the overhang amount threshold Wt based on the obtained overhang change amount ΔW, and use this for control of restricting the overhang amount W described above.

In the instrument manipulator 21, a portion of the instrument manipulator 21 advancing from the exit of the entry guide 9 to the body cavity may have a redundant degree of freedom. The elbow 263 and the shoulder 262 of the instrument manipulator 21 shown in FIG. 4A interlock such that the proximal link 265 (second proximal link 265b) and the distal link 267 remain parallel, and in a case where a pair of jaws do not operate independently, a portion of the instrument manipulator 21 advancing from the exit of the entry guide 9 into the body cavity has six degrees of freedom. In the instrument manipulator 21 shown in FIG. 4A, since a position of the wrist 27 is determined by the position and the posture of the surgical instrument 28, the overhang amount W of the elbow 263 may be large. In contrast, in the instrument manipulator 21 shown in FIG. 4B, a portion of the instrument manipulator 21 advancing from the exit of the entry guide 9 into the body cavity has seven degrees of freedom. One of the seven degrees of freedom is a redundant degree of freedom. In the instrument manipulator 21 shown in FIG. 4B, the posture of the instrument manipulator 21, by which the overhang amount W of the elbow 263 is suppressed by this redundant degree of freedom, can be obtained. Note that the degree of freedom can also be increased by operating the elbow 263 and the shoulder 262 independently or by operating a pair of jaws independently.

As described above, the instrument manipulator 21 is provided with a large number of rotation axes in a portion of the instrument manipulator 21 which advances from the exit of the entry guide 9 to the body cavity, and can take a complicated posture. Then, when the surgeon S manipulates a manipulator return command button (not shown) provided on the console 7, a large number of rotation axes of the instrument manipulator 21 return to a reference state. Specifically, when the console 7 receives input of a manipulator return manipulation by the manipulator return command button, in response to that, the slave controller 3 operates the robot main body 2 such that the instrument manipulator 21 takes a preset posture. At this time, the slave controller 3 may operate the robot main body 2 such that a portion other than the surgical instrument 28 takes a preset posture while the posture of the surgical instrument 28 is maintained. For example, as the preset posture, a posture in which a portion of the instrument manipulator 21 advancing from the exit of the entry guide 9 into the body cavity is linear may be employed.

In the surgical assist robot 1, in order to detect interference between a tissue in the body cavity of the patient P and the instrument manipulator 21, the instrument manipulator 21 is provided with a tactile sensor.

Figure 13:
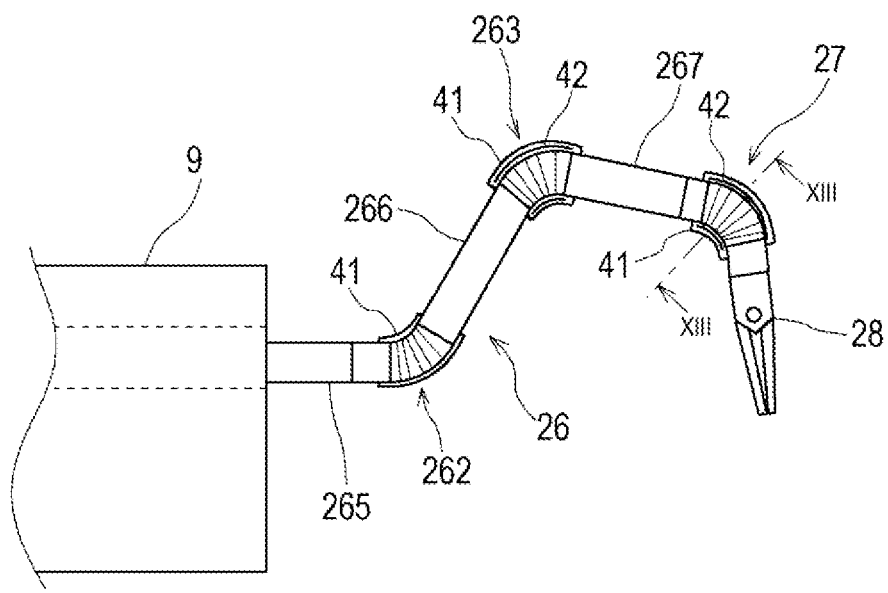
FIG. 13 is a diagram showing the wrist of the instrument manipulator including a tactile sensor.
Figure 14:
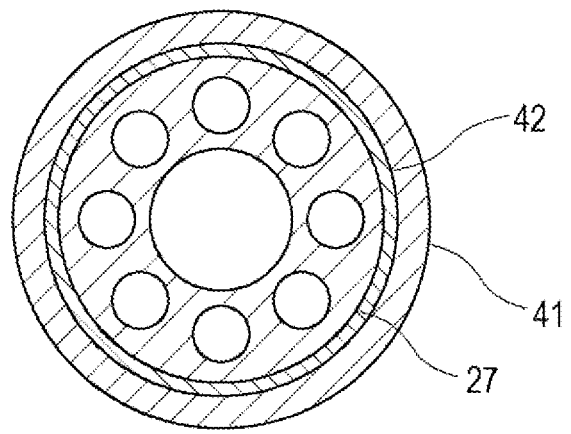
FIG. 14 is a cross-sectional view taken along line XIII-XIII in FIG. 13.
Figure 15:
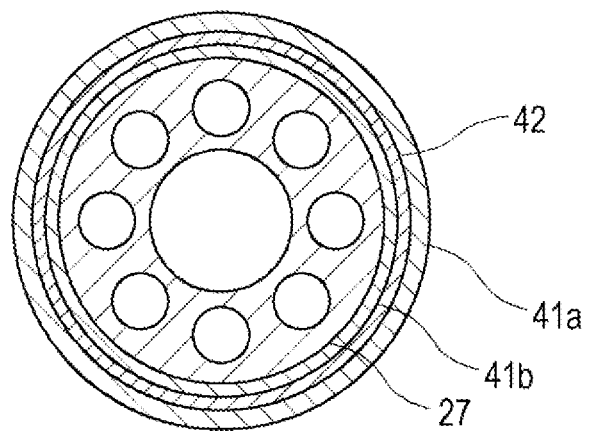
FIG. 15 is a view showing a variation of the tactile sensor shown in FIG. 14.
Figure 16:
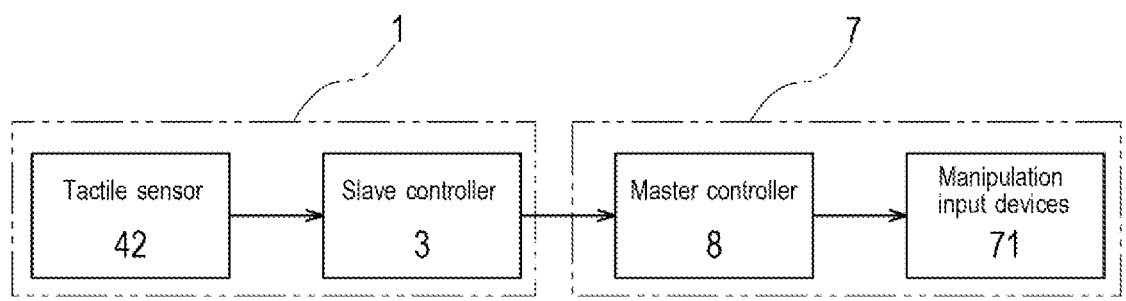
FIG. 16 is a diagram for describing flow of processing of generation of a signal from the tactile sensor.

FIG. 13 is a diagram showing the wrist 27, the elbow 263, and the shoulder 262 of the instrument manipulator 21 including a tactile sensor 42, FIG. 14 is a cross-sectional view taken along line XIII-XIII in FIG. 13, FIG. 15 is a diagram showing a variation of the tactile sensor shown in FIG. 14, and FIG. 16 is a diagram describing flow of processing of generation of a signal from the tactile sensor 42. As shown in FIGS. 13 and 14, the tactile sensor 42 is disposed on the outer periphery of a bending joint portion including the wrist 27, the elbow 263, and the shoulder 262. The tactile sensor may be disposed to cover the outer periphery of a joint portion. The tactile sensor 42 is a thin pressure-sensitive sensor called a tactile film sensor. The outer periphery of the tactile sensor 42 is covered with a sheath 41. The sheath 41 is flexible, and has a surface made from a slidable material. For the description of the sheath 41, US2012/0010628A1 is incorporated herein by reference. Note that, as shown in FIG. 15, the tactile sensor 42 may be provided between a double tube which consists of a sheath outer tube 41a and a sheath inner tube 41b. A publicly-known sensor, such as a capacitance type sensor or a piezoelectric element type sensor, can be employed as the tactile sensor.

As shown in FIG. 16, the tactile sensor 42 is connected to the slave controller 3 by a signal line passing through the inside of the instrument manipulator 21, and pressure detected by the tactile sensor 42 is output to the slave controller 3. The slave controller 3 compares the pressure detected by the tactile sensor 42 with a predetermined pressure upper limit value stored in advance. If the pressure detected by the tactile sensor 42 is equal to or higher than the pressure upper limit value, the slave controller 3 determines that there is a possibility that the instrument manipulator 21 interferes with a patient tissue, and performs predetermined processing. The predetermined processing performed by the slave controller 3 includes at least one of processing of outputting a warning to the console 7, processing of temporarily stopping the operation of the robot main body 2, processing of reducing a ratio (scale) of a displacement amount of the instrument manipulator 21 corresponding to the manipulation amount received by the console 7, and processing of outputting information to the console 7 such that a reaction force is applied to a manipulation force toward a radially outer side of the guide bore 90 received by the manipulation input device 71. As a value detected by the tactile sensor 42, a value (for example, a voltage value) correlated with the pressure may be employed instead of the pressure. The comparison between the value detected by the tactile sensor 42 and the predetermined threshold may be performed by the slave controller 3 or may be performed by a processor incorporated in the sensor.

The tactile sensor 42 also receives pressure from the sheath 41 and a plate-shaped member. Then, the pressure that the tactile sensor 42 receives from the sheath 41 and the plate-shaped member changes in accordance with a bending angle of the bending joint portion. Therefore, the pressure upper limit value may be a value that changes in accordance with a bending angle of the bending joint portion in which the tactile sensor 42 is provided. The slave controller 3 stores in advance predetermined information that associates the bending angle of the bending joint portion with the pressure upper limit value. The slave controller 3 obtains a pressure upper limit value corresponding to the bending angle of the bending joint portion obtained based on a manipulation amount of the manipulation cable by the drive disk, and uses this for the above control. The pressure upper limit value may be constant, and the pressure detected by the tactile sensor 42 may be corrected according to the pressure that the tactile sensor 42 receives from the sheath 41 or the plate-shaped member. In this case, the slave controller 3 stores in advance predetermined information that associates the bending angle of the bending joint portion with a correction value of the pressure detected by the tactile sensor 42. As described above, the value detected by the tactile sensor 42 may be compared with a predetermined threshold value in consideration of the pressure that the tactile sensor 42 receives from the sheath 41 or the plate-shaped member.

As described above, the surgical system 100 according to the present embodiment includes the robot main body 2, the slave controller 3 for controlling the robot main body 2, the display device 73 that displays an endoscopic image, and the manipulation input device 71 that receives input from the surgeon S, and transmits a command corresponding to the input to the slave controller 3. The robot main body 2 includes the entry guide 9 having the plurality of guide bores 90, an entry guide support device (the positioner 10) that supports the entry guide 9, the instrument manipulator 21 that has the surgical instrument 28 provided at its distal end and is inserted into one of the guide bores 90 of the entry guide 9, and the endoscope manipulator 31 that has the endoscopic camera 33 provided at its distal end and is inserted into another one of the guide bores 90 of the entry guide 9. The manipulation input device 71 includes an manipulation tool that receives input of a body cavity insertion manipulation. Then, in response to the input of the body cavity insertion manipulation received by the manipulation input device 71, the slave controller 3 operates the robot main body 2 such that the surgical instrument 28 advances from the exit of the entry guide 9 after the endoscopic camera 33 advances from the exit of the entry guide 9 and capturing by the endoscopic camera 33 is started.

Further, a method for controlling the surgical system 100 according to the present embodiment includes the steps of: receiving input of a body cavity insertion manipulation via the manipulation input device 71; causing the endoscopic camera 33 to advance from the exit of the entry guide 9 in response to the input of the body cavity insertion manipulation; causing the endoscopic camera 33 to start capturing; and causing the surgical instrument 28 to advance from the exit of the entry guide 9 after the endoscopic camera 33 starts capturing. Here, the step of causing the surgical instrument 28 to advance from the exit of the entry guide 9 may include causing the surgical instrument 28 to advance from the exit of the entry guide 9 in response to start of capturing by the endoscopic camera 33.

According to the surgical system 100 configured as described above and the method for controlling the surgical system 100, the surgeon S can perform manipulation of causing the surgical instrument 28 to advance from the entry guide 9 to the body cavity of the patient P while checking an endoscopic image captured by the endoscopic camera 33. In this manner, it is possible to assist the surgeon S in manipulating a surgical tool in such a manner as avoiding interference between the surgical instruments 28 and between the surgical instruments 28 and a patient tissue.

Further, in the surgical system 100 according to the present embodiment, the slave controller 3 operates the robot main body 2 such that a portion of the instrument manipulator 21 advancing from the exit of the entry guide 9 maintains a linear shape after the surgical instrument 28 starts to advance from the exit of the entry guide 9 until the surgical instrument 28 enters the field of view of the endoscopic camera 33.

Similarly, the method for controlling the surgical system 100 according to the present embodiment further includes a step of operating the instrument manipulator 21 such that a portion of the instrument manipulator 21 advancing from the exit of the entry guide 9 maintains a linear shape after the surgical instrument 28 starts to advance from the exit of the entry guide 9 until the surgical instrument 28 enters the field of view of the endoscopic camera 33.

According to the surgical system 100 and the method for controlling the surgical system 100, the surgeon S can easily estimate a position and a posture of the surgical instrument 28 when the surgical instrument 28 is out of the field of view of the endoscopic camera 33. In this manner, it is possible to assist the surgeon S in manipulating a surgical tool in such a manner as avoiding interference between the surgical instruments 28 and between the surgical instruments 28 and a patient tissue.

Further, in the entry guide 9 of the surgical system 100 according to the present embodiment, the distal end of the guide bore 90 into which the endoscope manipulator 31 is inserted may be positioned closer to the proximal side of the entry guide 9 than the distal end of the guide bore 90 into which the instrument manipulator 21 is inserted. In this case, the slave controller 3 may operate the robot main body 2 such that the surgical instrument 28 starting to advance from the exit of the entry guide 9 is in a state of being in the field of view of the endoscopic camera 33, and, while this state is maintained, the surgical instrument 28 advances from the exit of the entry guide 9.

Similarly, in the method for controlling the surgical system 100 according to the present embodiment, the step of causing the surgical instrument 28 to advance from the exit of the entry guide 9 may include causing the surgical instrument 28 starting to advance from the exit of the entry guide 9 to be in a state of being in the field of view of the endoscopic camera 33, and, while maintaining this state, causing the surgical instrument 28 to advance from the exit of the entry guide 9.

According to the entry guide 9, the exit from the entry guide 9 of the endoscope manipulator 31 is positioned closer to the distal side of the entry guide 9 than the exit from the entry guide 9 of the instrument manipulator 21. Accordingly, the posture of the endoscope manipulator 31 can be changed to put the instrument manipulator 21 which is about to advance from the entry guide 9 into the field of view of the endoscopic camera 33. Then, by putting the instrument manipulator 21 which is about to advance from the entry guide 9 into the field of view of the endoscopic camera 33, the surgeon S can manipulate movement of the surgical instrument 28 while checking the surgical instrument 28 starting to advance into the body cavity in an endoscopic image.

Further, in the surgical system 100 according to the present embodiment, the slave controller 3 obtains the overhang amount W of the instrument manipulator 21 toward a radially outer side of the guide bore 90 from the center line L0 of the guide bore 90 in which the instrument manipulator 21 is inserted. When the overhang amount W exceeds the predetermined overhang amount threshold Wt, the slave controller 3 performs at least one of processing of outputting a warning to the manipulation input device 71, processing of temporarily stopping the operation of the robot main body 2, processing of reducing a ratio (scale) of a displacement amount of the instrument manipulator 21 corresponding to a manipulation amount received by the manipulation input device 71, and processing of outputting information to the manipulation input device 71 such that a reaction force is applied to a manipulation force (manipulation force to increase the overhang amount W) to a radially outer side of the guide bore 90 received by the manipulation input device 71.

Similarly, the method for controlling the surgical system 100 according to the present embodiment further includes the steps of: obtaining the overhang amount W of the instrument manipulator 21 toward a radially outer side of the guide bore 90 from the center line L0 of the guide bore 90 in which the instrument manipulator 21 is inserted; and, when the overhang amount W exceeds the predetermined overhang amount threshold Wt, performing at least one of processing of outputting a warning to the manipulation input device 71, processing of temporarily stopping the operation of the robot main body 2, processing of reducing a ratio of a displacement amount of the instrument manipulator 21 corresponding to a manipulation amount received by the manipulation input device 71, and processing of outputting information to the manipulation input device 71 such that a reaction force is applied to a manipulation force to a radially outer side of the guide bore 90 received by the manipulation input device 71.

In the surgical system 100 and the method for controlling the surgical system 100, while the surgeon S is manipulating the surgical instrument, there is possibility that part of the instrument manipulator 21 in the body cavity, in particular, a portion projecting from the entry guide 9 of the instrument manipulator 21 is out of the field of view of the endoscopic camera 33. On the other hand, the predetermined processing performed by the slave controller 3 when the overhang amount W exceeds the overhang amount threshold Wt can cause the surgeon S to recognize that the overhang amount W is excessive. In this manner, it is possible to assist the surgeon S in manipulating a surgical tool in such a manner as avoiding interference between the surgical instruments 28 and between the surgical instruments 28 and a patient tissue.

Further, in the surgical system 100, the configuration may be such that the slave controller 3 obtains a change amount (the overhang change amount ΔW) per unit time of the overhang amount W, and obtains the overhang amount threshold Wt from the overhang change amount ΔW on the basis of a predetermined correspondence relationship in which the overhang amount threshold Wt becomes smaller as the overhang change amount ΔW becomes larger and uses the obtained overhang amount threshold Wt for control.

The magnitude of the overhang change amount ΔW represents the moving speed of the outermost point Pe of the instrument manipulator 21. Therefore, the larger the moving speed of the outermost point Pe, the smaller the overhang amount threshold Wt. Thus, the surgeon S can recognize that the overhang amount W is excessive at an earlier stage as the moving speed of the outermost point Pe is larger, and thus the overhang amount W overshooting the limit value Wlimit can be prevented.

Further, in the surgical system 100 according to the present embodiment, the instrument manipulator 21 has at least one bending joint in which the tactile sensor 42 is disposed on the periphery. When pressure detected by the tactile sensor 42 exceeds the predetermined pressure threshold, the slave controller 3 performs at least one of processing of outputting a warning to the manipulation input device 71, processing of temporarily stopping the operation of the robot main body 2, processing of reducing a ratio (scale) of a displacement amount of the instrument manipulator 21 corresponding to a manipulation amount received by the manipulation input device 71, and processing of outputting information to the manipulation input device 71 such that a reaction force is applied to a manipulation force that is received by the manipulation input device 71 and increases the overhang amount W.

As described above, in a case where the tactile sensor 42 detects a pressure exceeding a predetermined pressure threshold, the instrument manipulator 21 is likely to be in contact with another one of the instrument manipulators 21 or a patient tissue. In such a case, the surgeon S can be made aware of the possibility of contact by the predetermined processing performed by the slave controller 3. In this manner, it is possible to assist the surgeon S in manipulating a surgical tool in such a manner as avoiding interference between the surgical instruments 28 and between the surgical instruments 28 and a patient tissue.

Further, in the surgical system 100 according to the present embodiment, the instrument manipulator 21 includes the wrist 27 connected to the surgical instrument 28, the elbow 263 connected to the wrist 27 with the distal link 267 interposed therebetween, the shoulder 262 connected to the elbow 263 with the middle link 266 interposed therebetween, and the proximal link 265 connected to the shoulder 262.

Then, the shoulder 262 bendably and rotatably connects the middle link 266 and the proximal link 265, and the slave controller 3 restricts the bending movable range θs of the shoulder to the range (θ1) in which the middle link 266 is rotated toward the outer peripheral side of the entry guide 9 by 0 degrees or more and less than 90 degrees, and the range (θ2) in which the middle link 266 is rotated toward the inner peripheral side of the entry guide 9 by 0 degrees or more and less than 30 degrees, where an extension of the center line L1 of the proximal link 265 is set to 0 degrees.

This can prevent a patient tissue from being pinched between the instrument manipulator 21 and the entry guide 9 when the shoulder 262 is bent.

Furthermore, the wrist 27 bendably and rotatably connects the distal link 267 and the wrist 27, and the slave controller 3 restricts the bending movable range θw of the wrist 27 to the range (θ3) in which the surgical instrument 28 is rotated toward the inner peripheral side of the entry guide 9 by 0 degrees or more and less than 100 degrees where the extension of the center line L3 of the distal link 267 is set to 0 degrees.

In this manner, when the wrist 27 is bent, the surgical instrument 28 can be prevented from projecting significantly toward the outer side of the entry guide 9 or interfering with another one of the surgical instruments 28.

Further, the proximal link 265 includes the first proximal link 265a, the second proximal link 265b, and the auxiliary joint 261 that bendably and rotatably connecting the first proximal link 265a and the second proximal link 265b. The slave controller 3 restricts the operation of the auxiliary joint 261 such that it does not rotate during surgery after the surgical instrument 28 is inserted into the body cavity.

The auxiliary joint 261 may be positioned in a portion of the proximal link 265 which is not inserted into the entry guide 9. In this manner, when the instrument manipulator 21 is replaced, the proximal link 265 can be bent in two by the auxiliary joint 261. Accordingly, attaching and detaching work of the instrument manipulator 21 to and from the translation unit 22 is facilitated. Alternatively, the auxiliary joint 261 may be positioned in a portion of the proximal link 265 which advances from the exit of the entry guide 9. This facilitates positioning of the surgical instrument 28 near a body wall by bending the auxiliary joint 261 when the surgical instrument 28 is inserted into the body cavity.

Further, in the surgical system 100 according to the present embodiment, the surgical instrument 28 may be a forceps having the pair of jaws 281a and 281b which operate independently of each other.

In this manner, tips of the forceps can be opened and closed by simultaneously rotating the pair of jaws 281a and 281b in opposite directions. Further, by rotating the pair of jaws 281a and 281b in the same direction at the same time, an object can be moved while being gripped by the tips of the forceps.

Further, in the surgical system 100 according to the present embodiment, a portion of the instrument manipulator 21 that advances from the exit of the entry guide 9 may have six or more degrees of freedom, the manipulation input device 71 may include a manipulation tool that receives inputs of a manipulator return manipulation, and the slave controller 3 may operate the robot main body 2 such that a portion of the instrument manipulator 21 advancing from the exit of the entry guide 9 has a linear shape while maintaining the posture of the surgical instrument 28 in response to the inputs of the manipulator return manipulation received by the manipulation input device 71.

Similarly, the method for controlling the surgical system 100 according to the present embodiment may further include the steps of: receiving input of a manipulator return manipulation via the manipulation input device 71; and operating the instrument manipulator 21 such that a portion of the instrument manipulator 21 advancing from the exit of the entry guide 9 has a linear shape while maintaining the posture of the surgical instrument 28 in response to the input of the manipulator return manipulation.

Alternatively, in the surgical system 100 according to the present embodiment, a portion of the instrument manipulator 21 that advances from the exit of the entry guide 9 may have seven degrees of freedom, the manipulation input device 71 may include a manipulation tool that receives inputs of a manipulator return manipulation and the slave controller 3 may operate the robot main body 2 such that a portion of the instrument manipulator 21 advancing from the exit of the entry guide 9 has a linear shape while the posture of the surgical instrument 28 is maintained in response to the inputs of the manipulator return manipulation received by the manipulation input device 71.

In this manner, although a portion of the instrument manipulator 21 advancing from the exit of the entry guide 9 has a large number of movable axes, the instrument manipulator 21 can be returned to a basic posture while a posture of the surgical instrument 28 is maintained by simple manipulation.

Although the preferred embodiments of the present invention are described above, modifications of details of the specific structure and/or function details of the above-described embodiments may be included in the present invention without departing from the spirit of the present invention.

What is claimed is:

1. A surgical system comprising:
    a robot main body;
    a slave controller configured to control the robot main body;
    a display device configured to display an endoscopic image; and
    a manipulation input device configured to receive input from a surgeon and transmit a command corresponding to the input to the slave controller, the manipulation input device including a manipulation tool that receives input of a body cavity insertion manipulation command, wherein:
    the robot main body includes:
        an entry guide that has a first guide bore and a second guide bore;
        an entry guide support device that supports the entry guide;
        an instrument manipulator that has a surgical instrument provided at a distal end and is inserted into the first guide bore of the entry guide; and
        an endoscope manipulator that has an endoscopic camera provided at a distal end and is inserted into the second guide bore of the entry guide, and
    the slave controller is configured to:
        receive the body cavity insertion manipulation command via the manipulation tool;
        in response to receiving the body cavity insertion manipulation command, control the endoscope manipulator such that the endoscopic camera advances from an exit of the second guide bore and starts capturing images; and
        in response to the endoscopic camera advancing from the exit of the second guide bore and starting to capture the images, control the instrument manipulator such that the surgical instrument advances from an exit of the first guide bore.

2. The surgical system according to claim 1, wherein the slave controller controls the instrument manipulator such that a portion of the instrument manipulator advancing from the exit of the first guide bore maintains a linear shape after the surgical instrument starts to advance from the exit of the first guide bore until the surgical instrument enters a field of view of the endoscopic camera.

3. The surgical system according to claim 1, wherein:
    in the entry guide, a distal end of the second guide bore into which the endoscope manipulator is inserted is positioned closer to a proximal side of the entry guide relative to a distal end of the first guide bore into which the instrument manipulator is inserted, and
    the slave controller controls the robot main body so as to cause the surgical instrument that starts to advance from the exit of the first guide bore to be in a state of being in a field of view of the endoscopic camera, and cause the surgical instrument to advance from the exit of the first guide bore while maintaining the state.

4. The surgical system according to claim 1, wherein the slave controller obtains an overhang amount of the instrument manipulator toward a radially outer side of the first guide bore from a center line of the first guide bore in which the instrument manipulator is inserted, and, when the overhang amount exceeds a predetermined overhang amount threshold, the slave controller performs at least one of:
   processing of outputting a warning to the manipulation input device,
   processing of temporarily stopping operation of the robot main body,
   processing of reducing a ratio of a displacement amount of the instrument manipulator corresponding to a manipulation amount received by the manipulation input device, and
   processing of outputting information to the manipulation input device such that a reaction force is applied to a manipulation force to a radially outer side of the first guide bore received by the manipulation input device.

5. The surgical system according to claim 4, wherein the slave controller obtains a change amount per unit time of the overhang amount, and obtains the overhang amount threshold from the change amount based on a predetermined correspondence relationship such that the overhang amount threshold decreases as the change amount increases.

6. The surgical system according to claim 1, wherein the slave controller controls the endoscope manipulator such that the endoscopic camera starts capturing when the endoscopic camera is in the second guide bore and then the endoscopic camera advances from the exit of the second guide bore.

7. The surgical system according to claim 1, wherein the slave controller controls the endoscope manipulator such that the endoscopic camera advances from the exit of the second guide bore in response to start capturing by the endoscopic camera.

8. The surgical system according to claim 1, wherein:
   the instrument manipulator includes a first translation unit linearly moving a proximal end of the instrument manipulator such that the surgical instrument advances from the exit of the entry guide or retracts from the exit of the entry guide, and
   the endoscope manipulator includes a second translation unit linearly moving a proximal end of the endoscope manipulator such that the endoscopic camera advances from the exit of the second guide bore or retracts from the exit of the second guide bore.

9. The surgical system according to claim 1, wherein:
   the instrument manipulator includes a first wrist connected to the surgical instrument, a first arm connected to the first wrist at a distal end, and a first drive unit configured to drive the first wrist, and
   the endoscope manipulator includes a second wrist connected to the endoscopic camera, a second arm connected to the second wrist at a distal end, and a second drive unit configured to drive the second wrist.

10. The surgical system according to claim 9, wherein:
    the instrument manipulator includes a first transmission unit that transmits a driving force of the first drive unit to the first wrist, and
    the endoscope manipulator includes a second transmission unit that transmits a driving force of the second drive unit to the second wrist.

11. The surgical system according to claim 10, wherein the first transmission unit is detachably connected to the first drive unit and the second transmission unit is detachably connected to the second drive unit.

12. The surgical system according to claim 10, wherein the first transmission unit is detachably connected to the first drive unit through a first adapter, and the second transmission unit is detachably connected to the second drive unit through a second adapter.

13. The surgical system according to claim 10, wherein:
    the first transmission unit includes a first drive disc detachably connected to the first drive unit, and
    the second transmission unit includes a second drive disc detachably connected to the second drive.

14. The surgical system according to claim 9, wherein:
    the first arm includes a first bending joint connecting to the first wrist, and
    the second arm includes a second bending joint connecting to the first wrist.

15. A surgical system comprising:
a robot main body;
a slave controller configured to control the robot main body; and
a manipulation input device configured to receive input of a command from a surgeon and transmit the command to the slave controller,
wherein:
the robot main body includes:
   an entry guide having first and second guide bores;
   an instrument manipulator that has a surgical instrument provided at a distal end and is inserted into the first guide bore of the entry guide; and
   an endoscope manipulator that has an endoscopic camera provided at a distal end and is inserted into the second guide bore of the entry guide,
the slave controller is configured to:
   receive the body cavity insertion command via the manipulation input device;
   in response to receive the body cavity insertion command, control the endoscope manipulator such that the endoscopic camera advances from an exit of the second guide bore and starts capturing; and
   in response to the endoscopic camera advancing from the exit of the second guide bore and starting to capture, control the instrument manipulator such that the surgical instrument advances from an exit of the first guide bore.

16. The surgical system according to claim 15, wherein the slave controller controls the instrument manipulator such that a portion of the instrument manipulator advancing from the exit of the first bore maintains a linear shape after the surgical instrument starts to advance from the exit of the first bore until the surgical instrument enters a field of view of the endoscopic camera.

17. The surgical system according to claim 15, wherein the slave controller controls the endoscope manipulator such that the endoscopic camera advances from the exit of the second guide bore in response to start capturing by the endoscopic camera.

18. The surgical system according to claim 15, wherein:
    the instrument manipulator includes a first translation unit linearly moving a proximal end of the instrument manipulator such that the surgical instrument advances from the exit of the entry guide or retracts from the exit of the entry guide, and
    the endoscope manipulator includes a second translation unit linearly moving a proximal end of the endoscope manipulator such that the endoscopic camera advances from the exit of the second guide bore or retracts from the exit of the second guide bore.

19. The surgical system according to claim 15, wherein:
    the instrument manipulator includes a first wrist connected to the surgical instrument, a first arm connected to the first wrist at a distal end, and a first drive unit configured to drive the first wrist, and the endoscope manipulator includes a second wrist connected to the endoscopic camera, a second arm connected to the second wrist at a distal end, and a second drive unit configured to drive the second wrist.

20. The surgical system according to claim 19, wherein:

the instrument manipulator includes a first transmission unit that transmits a driving force of the first drive unit to the first wrist, and the endoscope manipulator includes a second transmission unit that transmits a driving force of the second drive unit to the second wrist.

\* \* \* \* \*